United States Patent [19]

Glaser

[11] Patent Number: Plant 5,917

[45] Date of Patent: Mar. 31, 1987

[54] AZALEA PLANT NAMED CHARLY

[76] Inventor: Karl Glaser, Stadtteil Harreshausen, Ausserhalb 25, 6113 Babenhausen 5, Fed. Rep. of Germany

[21] Appl. No.: 699,458

[22] Filed: Feb. 7, 1985

[51] Int. Cl.[4] ..... A01H 5/00

[52] U.S. Cl. ..... Plt./57

[58] Field of Search ..... Plt./55–57

*Primary Examiner*—Robert E. Bagwill

*Attorney, Agent, or Firm*—Schwartz, Jeffery, Schwaab, Mack, Blumenthal & Evans

[57] ABSTRACT

An azalea plant named Charly characterized by its red flower color, very large flowers which are semi-double in form, excellent growth habit, ease of propagation, early response, and its ability to grow and blossom at relatively low temperatures.

2 Drawing Figures

The present invention comprises a new and distinct cultivar of Rhododendron L, commonly referred to as azalea, and known by the cultivar name Charly.

In 1972, applicant began a planned breeding program in Babenhausen, Federal Republic of Germany, which program had the general objective of creating new azalea cultivars having early response and having the capability of developing and blossoming at relatively low temperatures, for example, temperatures as low as in the range of 5°–6° C. A further objective of the breeding was to develop a cultivar having relatively intense pink flower color. These desired characteristics in combination were not present or were in need of improvement in previously available commercial cultivars.

The breeding program above described resulted in the cultivar Luci, an intense pink color azalea disclosed in applicant's pending application.

The new cultivar Charly was discovered by me in 1978 as a mutation of Luci, growing in a group of plants of the parent cultivar in a greenhouse in Babenhausen, Federal Republic of Germany. The distinctly darker blossom color, tending more toward scarlet than pink, was immediately apparent. Asexual reproduction of the new cultivar was accomplished when vegetative cuttings were taken by me later in 1978 in a controlled greenhouse environment in Babenhausen, Federal Republic of Germany. Subsequent examination demonstrated that the combination of characteristics as herein disclosed for Charly are firmly fixed and are retained through successive generations of asexual reproduction.

Charly has not been observed under all possible environmental conditions. The phenotype may vary significantly with variations in environment such as temperature, light intensity, and day length, and may also vary through the application of growth regulators. The following description is based on plants of the new cultivar grown in Babenhausen, Federal Republic of Germany under greenhouse conditions which approximate those generally used in commercial practice.

The traits listed below have been repeatedly observed and are determined to be basic characteristics of Charly, which in combination distinguish this azalea as a new and distinct cultivar. It should be noted that except for its substantially darker flower color, Charly is similar in most respects to its parent cultivar Luci.

(1) Red flower color, and a floriferous flowering habit.

(2) Blossoms are semi-double in form, and very large, reaching a diameter of up to 12 cm. The size of the blossoms depends on when the plant is pinched, how the plants are nourished, and the growing conditions, e.g. light intensity and day length. Growth regulators such as alar can reduce blossom size by up to one third.

(3) Easy to propagate, with the roots of the cuttings developing quickly.

(4) With proper pinching, a symmetrical and relatively large, yet compact, plant is developed.

(5) Excellent growth habit, even during the low light and low temperature conditions of winter greenhouse cultivation.

(6) Early response, with plants having buds showing color and ready to be sold in as little as approximately 130 days after pinching, during high light periods. Low light and temperature conditions, and the use of growth regulators, e.g. alar, can delay flowering several weeks.

(7) The early response is not significantly affected by low temperation. Although temperatures such as 5°–6° C. slow the development and response to some extent, the low temperature response of Charly is excellent compared to existing varieties. From an energy standpoint, this is a significant characteristic.

(8) Color intensity is strongest during August to October. With shorter days, the color is somewhat faded. The blossoms retain their color for approximately 14 days before fading, but remain attractive for 3–6 weeks.

The accompanying photographic drawings show typical inflorescence and foliage characteristics of Charly, with the colors being as nearly true as possible with illustrations of this type. At the top of sheet 1 is a color photograph of Charly, in top perspective view in pot form. At the bottom of sheet 1 is a comparison color photograph, in plan view, showing typical blossoms of Luci and Charly. The flower color of Charly as depicted in the comparison photograph is slightly more red than the actual flower color, which appears in the top perspective view. However, the color values stated below are correct.

In the following description, color references are made to The Royal Horticultural Society Colour Chart, and were taken in Babenhausen, Federal Republic of Germany.

Classification:

*Botanical.*—Rhododendron L, cv Charly.

*Commercial.*—Pot azalea.

PLANT

Growth habit: Good to excellent, developing rapidly and symmetrically with adequate pinching into a wide and bushy plant with average compactness. Requires pinching earlier and more often than other azalea cultivars of this general type, with 3–5 pinches producing a symmetrical and relatively large plant. The cultivar is particularly resistant to low temperatures, growing well even during winter conditions of low light and low temperatures in the range of 5°–6° C.

Branching: Satisfactory to very good. After the first pinching, young shoots begin to grow quite rapidly early, and in large quantities, particularly after additional pinchings.

Response period: The response period is very short for this type of cultivar. The response varies considerably depending upon light and temperature conditions, and the application of growth regulators. For plants pinched in mid-May for the first time, plants having buds showing color and ready to be sold are available approximately 130–135 days later. Where growth is under less light and lower temperature conditions, the response period may be up to 130–150 days, and the application of alar for growth regulation can delay the response period for up to 7–8 weeks.

Ease of propagation: Good to very good. Cuttings root quickly and firmly.

Buds: Generally elliptical in shape. Plant may be cultivated without break and blossoms regularly. A particular advantage of the cultivar is that bud development proceeds in low temperature conditions, for example, at approximately 5° C. This low temperature development is not common to most azalea varieties of this type. But development is faster at higher temperatures.

Leaves: Young shoots are green to reddish in color, changing to a mid-green in young and a darker green in fully grown leaves; color under surface of young leaves is light green, and mid-green on fully grown leaves. Fully grown leaves are convex, and generally oval in shape, terminating in a rounded point. The fully grown leaves are slightly shiny on the top surface, and the overall length and width of the fully grown leaves are generally average for this type of azalea.

BLOSSOM

Shape and size: The blossoms have the shape of a wide horn, and are semi-double and very large, reaching a diameter of up to 12 cm. The diameter of the blossoms depends on the extent of pinching, growing conditions, and nourishment. Generally speaking, late pinching and low light conditions will result in blossoms having a relatively smaller diameter. The blossoms tend to reach their greatest diameter during periods of high light and long day length. The diameter of the blossoms are adversely affected by growth regulation, such as treatments with alar, which treatment is recommended only for small plants. The blossoms are carried on relatively long stems, 1.0 to 1.5 cm., and in view of the size and form of the blossom, there is a tendency for the blossom to hang or bend somewhat on the stem. This characteristic can be controlled by pinching.

Color: The color is red 53D on the top and under surfaces of the blossoms, with red spots a little darker than 58B appearing irregularly on the petals. The throat of the blossom is a somewhat brighter 58B on the inside (top), and somewhat lighter than 58B on the outside (bottom).

Temperature tolerance: The development and maturing of the blossoms is not significantly impeded at relatively low temperatures, an important characteristic of the cultivar, although optimum temperatures for blossoming is in the range of 12°–18° C., having regard to energy costs and optimum blossom characteristics. For example, during the period from November to January, the time for developing blossoms from buds showing color was approximately 16 days at approximately 15° C.

Normal blossoming period: From the end of August to mid-November, although year around flowering is achieved by greenhouse cultivation.

Blossom life: Blossoms hold their red flower color for approximately 14 days, after which the blossoms begin to fade in color. The intensity and luminosity of the red color is strongest from August to October, and as the days get shorter, the red blossom color is somewhat less intense. The blossoms remain attractive for approximately 3–6 weeks, depending upon geographical location and season.

Corona: Relatively long, 5 in number, with the tip of the corona being relatively wide.

Reproductive organs: The reproductive organs of Charly are not distinctive.

I claim:

1. A new and distinct cultivar of azalea plant named Charly, as described and illustrated, and particularly characterized by its red flower color, very large flowers which are semi-double in form, excellent growth habit, ease of propagation, early response, and its ability to grow and blossom at relatively low temperatures.

* * * * *

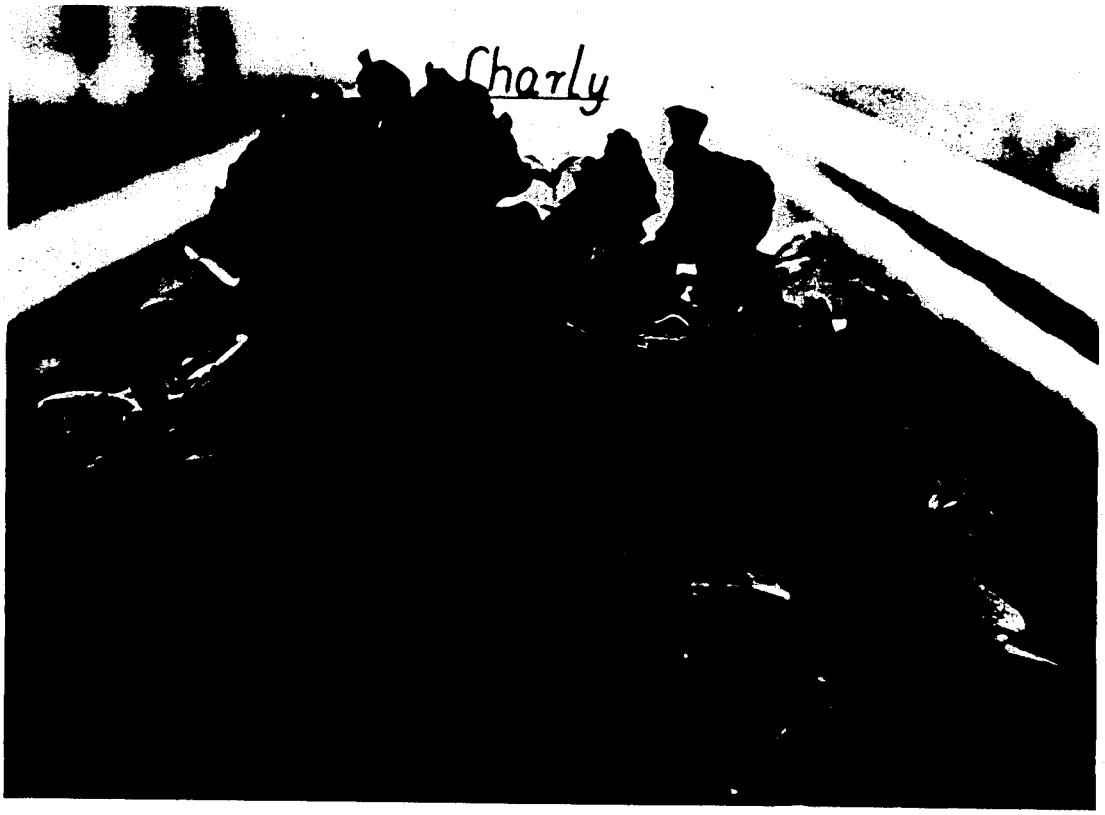
Charly
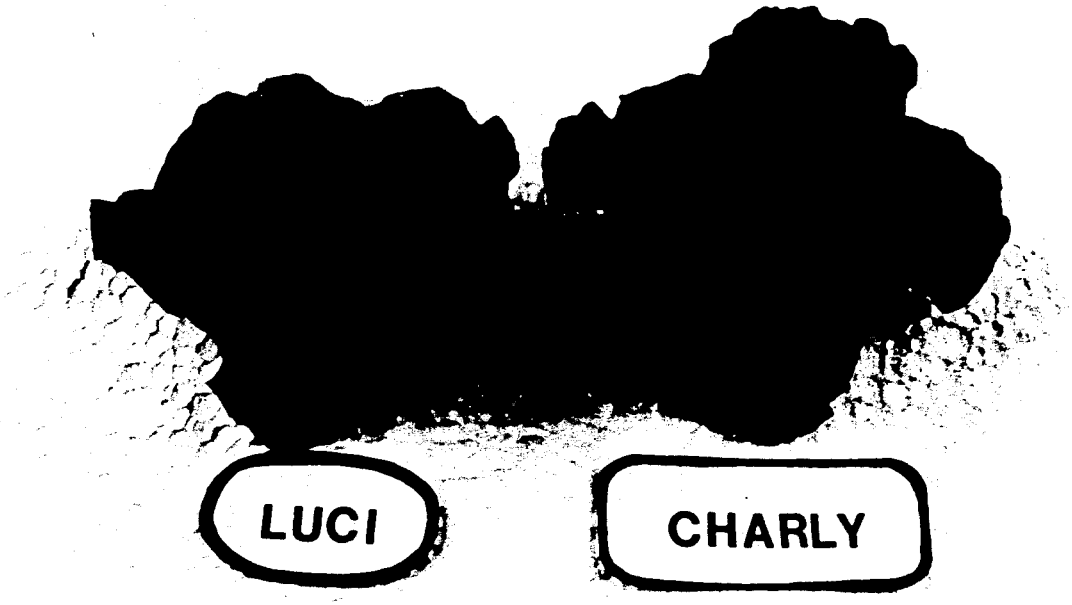
LUCI
CHARLY